United States Patent [19]

Staffe et al.

[11] 4,127,735

[45] Nov. 28, 1978

[54] PREPARATION OF DICHLOROPHENE

[75] Inventors: Adolf Staffe, Leverkusen;
Klaus-Friedrich Lehment, Odenthal;
Wilhelm Backhaus, Cologne, all of Germany

[73] Assignee: Bayer Aktiengesellschaft, Leverkusen, Germany

[21] Appl. No.: 737,746

[22] Filed: Nov. 1, 1976

[30] Foreign Application Priority Data

Nov. 17, 1975 [DE] Fed. Rep. of Germany ....... 2551498

[51] Int. Cl.$^2$ ...................... C07C 37/00; C07C 37/20; C07C 39/16
[52] U.S. Cl. .................................................... 568/726
[58] Field of Search .................................... 260/619 A

[56] References Cited

U.S. PATENT DOCUMENTS

| 2,334,408 | 11/1943 | Gump et al. | 260/619 A |
| 3,057,928 | 10/1962 | Koblitz et al. | 260/619 A |
| 3,426,081 | 2/1969 | Shore et al. | 260/619 A |

FOREIGN PATENT DOCUMENTS 1,208,325  10/1970  United Kingdom ................ 260/619 A

*Primary Examiner*—Norman Morgenstern
*Attorney, Agent, or Firm*—Sprung, Felfe, Horn, Lynch & Kramer

[57] ABSTRACT

An improvement in a process for the preparation of dichlorophene by reacting p-chlorophenol with formaldehyde in the presence of sulfuric acid. The improvement lies in contacting p-chlorophenol with the stoichiometric excess of formaldehyde in aqueous sulfuric acid by introducing into a sulfuric acid reaction medium 1 to 6% by weight of the total amount of p-chlorophenol to be reacted and thereafter adding the formaldehyde and additional p-chlorophenol to the reaction mixture in an amount such that at the end of the addition of the p-chlorophenol only 85 to 98% by weight of the total amount of formaldehyde has been added. The balance of the formaldehyde is then introduced into the reaction mixture.

13 Claims, No Drawings

PREPARATION OF DICHLOROPHENE

BACKGROUND OF THE INVENTION

1. Field of the invention

The invention relates to a process for the preparation of dichlorophene (5,5'-dichloro-2,2'-dihydroxydiphenylmethane) from p-chlorophenol and formaldehyde in sulphuric acid.

2. Discussion of Prior Art

Because of its microbicidal action, dichlorophene is used as an industrial preservative, for example for industrial woollen goods, heavy fabrics and cooling lubricants. In hygiene and medicine, it is used as an antiseptic and anthelmintic (British Pharmacopeia 1973, page 157).

In selecting a process of preparation, it is necessary to take into account the purity standards relating to the particular end use of the dichlorophene. For use as an industrial preservative, a residual content of p-chlorophenol of at most 0.8% is desired. Furthermore, it is advantageous if concentrated, residue-free solutions in aqueous sodium hydroxide solution or in an alcohol, such as butanol can be prepared. Inadequate solubility is in most cases due to an excessive content of products of higher molecular weight from side reactions. Where the preservation of non-coloured products such as, for example, paper is concerned, a low intrinsic colour of the dichlorophene is desirable in addition.

For the hygiene field and the veterinary medicine field, a p-chlorophenol content of less than 0.1% is required for toxicological reasons (British Pharmacopoeia 1973, page 156 to 157, British Veterinary Codex 1965, page 134).

To assess the purity of the dichlorophene, and assess the p-chlorophenol content, it is possible to employ not only the solubility in aqueous alkali or in alcohols, but also the melting point. Chemically pure dichlorophene melts at 177° to 178° C.

The melting point is lowered particularly by the presence of p-chlorophenol and other impurities of a low molecular weight. German Reich Patent No. 530,219 has disclosed the manufacture of dichlorophene by reacting p-chlorophenol with formaldehyde in the molar ratio of 2 : 0.96 to 1.09 in 50% strength sulphuric acid at 50° to 65° C. It is true that no data regarding the purity of the dichlorophene obtained are given in German Reich Patent No. 530,219, but the dichlorophene prepared in accordance with the instructions of this patent specification is dark in colour and contains unconverted p-chlorophenol and more highly condensed by-products which are detrimental to the solubility. A crude product obtained in this way is therefore unsuitable for industrial use. The unconverted p-chlorophenol can be removed by steam distillation, whereby the intrinsic colour of the crude product becomes even deeper. The dark-coloured and the sparingly soluble more highly condensed reaction products can be removed afterwards by clarification of an aqueous solution of the sodium salt of dichlorophene and reprecipitation of the purified dichlorophene with mineral acids.

The disadvantages of the process described above are avoided, according to U.S. Pat. No. 2,334,408, by carrying out the condensation in methanol as the solvent, with concentrated sulphuric acid as the catalyst, at temperatures of −10° to 0° C. According to British Pat. No. 1,208,325, an improvement in this process is achieved by a continuous operation under similar reaction conditions, the amount of formaldehyde required for the condensation being supplied stepwise to the reaction mixture over the course of a three-step kettle cascade. The continuous method in this case essentially serves to give improved heat control of the process of preparation. The dichlorophene can be precipitated from the reaction mixture by dilution with water, in a purity which permits its use as an industrial preservative. The melting point of the dichlorophene prepared in this way is 165° to 167° C; the yields, based on the p-chlorophenol employed, are 90 to 93% of theory.

Compared to the method of German Reich Patent No. 530,219, the latter processes admittedly give a dichlorophene which is usable industrially without additional purification steps, but the use of solvents leads to additional problems in working up. Furthermore, the methanol/sulphuric acid mixture is diluted with water, as a result of the precipitation of the dichlorophene, to such an extent that a direct reuse for condensation is impossible.

It is a feature common to all the processes described above that the total amount of p-chlorophenol is added at the start of the reaction and the formaldehyde is only employed in a molar ratio of up to 0.505, relative to the p-chlorophenol. The large excess of p-chlorophenol established at least in the main stage of the reaction is considered essential in order to restrict excessive formation of higher molecular byproducts (British patent specification No. 1,208,325).

SUMMARY OF THE INVENTION

Broadly, this invention contemplates a process for the preparation of dichlorophene which comprises contacting p-chlorophenol with stoichiometric excess of formaldehyde in aqueous sulfuric acid in substantial absence of oxygen, at a reaction temperature of 45° to 75° C, by introducing into a sulfuric acid reaction mixture 1 to 6% by weight of the total amount of p-chlorophenol to be reacted and thereafter adding formaldehyde and additional p-chlorophenol to the reaction mixture in an amount such that at the end of the p-chlorophenol addition only 85 to 98% by weight of the total amount of formaldehyde has been added and thereafter adding the remaining formaldehyde. Generally speaking, the sulfuric acid employed is a 40 to 70% strength by weight $H_2SO_4$.

The process is generally conducted by introducing into a reaction mixture substantially free of oxygen and consisting essentially of the aqueous sulfuric acid the first 1 to 6% by weight of p-chlorophenol to be reacted. Thereafter, the formaldehyde addition is commenced together with additional p-chlorophenol. The addition of the formaldehyde and additional p-chlorophenol is performed up until all of the p-chlorophenol has been added, at which time only 85 to 98% of the total amount of formaldehyde should have been added. The addition of the additional p-chlorophenol and the formaldehyde can be performed by adding the same at constant ratio to the reaction mixture.

A process for the preparation of dichlorophene by reaction of p-chlorophenol with formaldehyde in sulphuric acid has now been found, in which, staggered in time, first the p-chlorphenol and then, the formaldehyde are introduced into the process, at elevated temperature and with oxygen being excluded essentially.

The process according to the invention can be explained by the following equation:

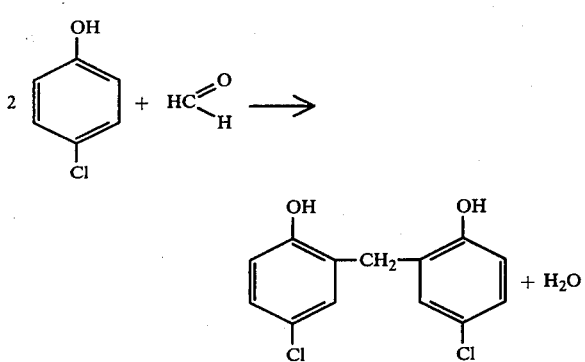

According to the process of the invention, the p-chlorophenol and the formaldehyde are employed in the reaction staggered in time. The p-chlorophenol and the formaldehyde are each reacted over a period of 5 to 50 hours, preferably 8 to 15 hours, and are run in at a constant ratio. At the beginning of the reaction, 1 to 6%, preferably 3 to 4%, of the total amount of the p-chlorophenol are introduced, and then the formaldehyde is added in such a way that at the end of the addition of the p-chlorophenol only 85 to 98%, preferably 90 to 95%, of the total amount of formaldehyde have been added. The remaining amount of formaldehyde is then introduced, the rate of running in being kept essentially unchanged.

The p-chlorophenol and the formaldehyde are employed in a molar ratio of 2:1.01 to 1.09, preferably 2:1.02 to 1.05, in the process according to the invention.

The p-chlorophenol is in general employed in the reaction at above its melting point, at about 50° to 70° C, in the commercially used (or available) technical purity, and without dilution. The formaldehyde can be used in 30 to 44% strength by weight aqueous solution, if appropriate stabilised with methanol or other commercially usual additives.

The reaction according to the process of the invention is carried out in sulphuric acid. In general, sulphuric acid of 40 to 70% strength by weight, preferably of 50 to 60% strength by weight, can be used.

An upper limit on the total concentration of the reactants in the sulphuric acid is imposed by the mechanical flow properties of the dichlorophene suspension obtained after the end of the reaction and by the dilution of the sulphuric acid by the water added with the formaldehyde solution and by the water produced in the reaction. Advantageously, the amount of the starting materials is so chosen that at the end of the reaction the suspension contains 15 to 30% by weight, preferably 20 to 25% by weight, of dichlorophene.

The process according to the invention can be carried out in the temperature range of 45° to 75° C, preferably of 50° to 60° C.

The process according to the invention is carried out with substantial exclusion of oxygen. Substantial exclusion of oxygen is achieved, for example, if the oxygen content of the gas phase above the reaction is less than 0.1% by volume. The exclusion of oxygen in accordance with the process of the invention can be effected, for example, by blanketing the reaction mixture with a protective gas, for example nitrogen.

The process according to the invention can be carried out, for example, as follows:

The sulphuric acid is first introduced into the reaction vessel and is heated to the reaction temperature. In order to exclude oxygen, the reaction mixture is blanketed with a protective gas. The p-chlorophenol and the aqueous formaldehyde solution are added, staggered in time, at a constant ratio.

The reaction in general lasts 5 to 50 hours, preferably 8 to 15 hours.

After completion of the reaction, the dichlorophene is separated from the sulphuric acid, for example by filtration, washed with water and dried.

After replacing the deficient amounts of acid and water, the sulphuric acid can be reused in a new reaction.

The dichlorophene obtainable according to the process of the invention in general contains 0.5 to 0.8% of p-chlorophenol. The melting point is above 172° C. In 10% sodium hydroxide solution, the product dissolves to the extent of at least 50% by weight, without leaving a residue. In butanol, the insoluble residue of a 40% strength by weight solution is less than 0.5% by weight. The purity accordingly corresponds to the standards demanded for use as a technical preservative.

In order to fulfil the conditions associated with use as a pharmaceutical preparation, the dichlorophene prepared according to the process of the invention merely has to be recrystallised, in a simple manner which is in itself known, from an aprotic solvent such as, for example, toluene (U.S. Pat. No. 2,334,408, British patent specification No. 1,208,325).

A further advantage of the process according to the invention is that the dichlorophene precipitates from the reaction mixture, from the beginning, in a crystalline form, so that the suspension remains free from lumps and the addition of seeding crystals is unnecessary.

EXAMPLE 1

A mixture of 300 kg of water and 405 kg of 96% strength by weight sulphuric acid is initially introduced into a 2 m³ kettle. The kettle is flushed with nitrogen at a temperature of 50° to 55° C, and is closed. 200 kg of p-chlorophenol and 88 kg of a 30% strength by weight aqueous formaldehyde solution are now metered in, over about 9 hours, at a constant ratio, under an excess pressure of nitrogen of at most 0.8 bar, in accordance with the following time plan:

In the first 15 minutes, 8.0 kg of p-chlorophenol are metered in, and thereafter the simultaneous addition of formaldehyde and p-chlorophenol is started. After about 8 hours, 200 kg of p-chlorophenol and 80 kg of formaldehyde have been introduced. The remaining 8 kg of formaldehyde are added over the course of 1 hour.

After the metering-in, the mixture is stirred for a further 5 hours and the product is then filtered off from the sulphuric acid. The sulphuric acid obtained from the filtration can be stocked up with fresh concentrated sulphuric acid and be employed in the next batch.

The reaction product is washed neutral with 3,500 kg of water and is dried in vacuo at 70° C.

Yield: 208 kg of dichlorophene (which corresponds to a yield of 99%, relative to the p-chlorophenol employed.)

What is claimed is:

1. A process for the preparation of dichlorophene which comprises contacting p-chlorophenol with a stoichiometric excess of formaldehyde in aqueous sulfuric acid in substantial absence of oxygen, at a reaction temperature of 45° to 75° C., by introducing into a sulfuric acid reaction mixture containing 40 to 70% strength by weight sulfuric acid 1 to 6% by weight of the total amount of p-chlorophenol to be reacted and thereafter adding formaldehyde and additional p-chlorophenol to the reaction mixture in amounts such that at the end of the p-chlorophenol addition only 85 to 98% by weight of the total amount of formaldehyde has been added and thereafter adding the remaining formaldehyde.

2. A process according to claim 1 wherein following the introduction of the 1–6% by weight of p-chlorophenol, p-chlorophenol and formaldehyde are added to the reaction mixture in admixture with one another.

3. A process according to claim 1 wherein following the introduction of the 1–6% by weight p-chlorophenol additional p-chlorophenol and formaldehyde are added to the reaction mixture at a constant ratio.

4. A process according to claim 1 wherein prior to the addition of the 1–6% by weight of p-chlorophenol the reaction mixture is substantially free of p-chlorophenol.

5. A process according to claim 1 wherein the reaction mixture is rendered substantially free of oxygen by blanketing the reaction mixture with a protective gas.

6. A process according to claim 1 wherein the p-chlorophenol and formaldehyde are reacted in a mol ratio of 2:1.01 – 1.09.

7. A process according to claim 1 wherein the p-chlorophenol and formaldehyde are employed in a molar ratio of 2:1.02 – 1.05.

8. A process according to claim 1 wherein the formaldehyde is employed in the form of a 30–44% by weight aqueous solution.

9. A process according to claim 1 wherein to a reaction mixture substantially free of p-chlorophenol there is initially added 3 to 4% by weight of p-chlorophenol to be reacted and additional p-chlorophenol and formaldehyde is thereafter added such that after all of the p-chlorophenol has been added only 90–95% by weight of the total amount of formaldehyde to be added has been introduced into the reaction mixture.

10. A process according to claim 1 wherein the reaction is conducted for a period of time between 5 and 15 hours.

11. A process according to claim 10 wherein the process is carried out over a period of 8 to 15 hours.

12. A process for the preparation of dichlorophene which comprises contacting p-chlorophenol with a stoichiometric excess of formaldehyde in aqueous sulfuric acid in substantial absence of oxygen, at a reaction temperature of 45° to 75° C., by introducing into a sulfuric acid reaction mixture consisting essentially of 40 to 70% strength by weight sulfuric acid 1 to 6% by weight of the total amount of p-chlorophenol to be reacted and thereafter adding formaldehyde and additional p-chlorophenol to the reaction mixture in amounts such that at the end of the p-chlorophenol addition only 85 to 98% by weight of the total amount of formaldehyde has been added and thereafter adding the remaining formaldehyde.

13. A process for the preparation of dichlorophene which comprises contacting p-chlorophenol with a stoichiometric excess of formaldehyde in aqueous sulfuric acid in substantial absence of oxygen, at a reaction temperature of 45° to 75° C., by introducing into a sulfuric acid reaction mixture consisting of 40 to 70% strength by weight sulfuric acid 1 to 6% by weight of the total amount of p-chlorophenol to be reacted and thereafter adding formaldehyde and additional p-chlorophenol to the reaction mixture in amounts such that at the end of the p-chlorophenol addition only 85 to 98% by weight of the total amount of formaldehyde has been added and thereafter adding the remaining formaldehyde.

* * * * *